US011534613B2

(12) United States Patent
Pflug et al.

(10) Patent No.: US 11,534,613 B2
(45) Date of Patent: Dec. 27, 2022

(54) WIRELESS POWER TRANSFER FOR MEDICAL DEVICES

(71) Applicant: ONWARD MEDICAL N.V., Eindhoven (NL)

(72) Inventors: Hans Pflug, Eindhoven (NL); Jeroen Tol, Eindhoven (NL); Koen Weijand, Alicante (ES)

(73) Assignee: Onward Medical N.V., Eindhoven (NL)

( * ) Notice: Subject to any disclaimer, the term of this patent is extended or adjusted under 35 U.S.C. 154(b) by 223 days.

(21) Appl. No.: 16/786,239

(22) Filed: Feb. 10, 2020

(65) Prior Publication Data
US 2020/0254265 A1 Aug. 13, 2020

(30) Foreign Application Priority Data
Feb. 9, 2019 (DE) .................... 10 2019 000 915.0

(51) Int. Cl.
*H02J 7/00* (2006.01)
*A61N 1/378* (2006.01)
(Continued)

(52) U.S. Cl.
CPC .............. *A61N 1/3787* (2013.01); *H02J 7/02* (2013.01); *H02J 50/12* (2016.02); *H02J 50/23* (2016.02); *H02J 50/27* (2016.02)

(58) Field of Classification Search
CPC ......... A61N 1/3787; A61N 1/378; H02J 7/02; H02J 50/12; H02J 50/23; H02J 50/27
(Continued)

(56) References Cited

U.S. PATENT DOCUMENTS 4,798,982 A * 1/1989 Voorman ............... H04B 1/586
327/362
5,876,425 A 3/1999 Gord et al.
(Continued)

FOREIGN PATENT DOCUMENTS

EP 2868343 A1 5/2015

OTHER PUBLICATIONS

Pflug et al., "Parallel Resonant Inductive Wireless Power Transfer", IEEE, Jun. 2019, pp. 182-187.*
(Continued)

*Primary Examiner* — Brian Ngo
(74) *Attorney, Agent, or Firm* — Finnegan, Henderson, Farabow, Garrett & Dunner LLP

(57) ABSTRACT

Inductive wireless power transfer systems are provided for medical devices, such as implantable medical devices (IMDs). The systems may comprise a transmitter unit and a receiver unit and may be configured for transferring power and/or signals from the transmitter unit to the receiver unit and/or vice versa. The transmitter unit may comprise an energy source, a transmitter antenna, and a supply line connected in between the energy source and the antenna. The receiver unit may comprise a receiver antenna and a rectifier output. The transmitter antenna and the receiver antenna may be configured to provide a wireless power transfer link. The supply line may comprise a virtual resistance unit, which may be configured to provide a virtual resistance, which may be determined such that the rectifier output provides a substantially constant or less varying charge current over a predetermined distance range, for a large range of implant depths.

12 Claims, 7 Drawing Sheets

(51) Int. Cl.
*H02J 50/12* (2016.01)
*H02J 50/23* (2016.01)
*H02J 50/27* (2016.01)
*H02J 7/02* (2016.01)

(58) Field of Classification Search
USPC .................. 320/106, 107, 108, 109, 110
See application file for complete search history.

(56) References Cited

U.S. PATENT DOCUMENTS

| | | | |
|---|---|---|---|
| 6,901,292 B2 | 5/2005 | Hrdlicka et al. | |
| 7,801,600 B1 | 9/2010 | Carbunaru et al. | |
| 7,813,809 B2 | 10/2010 | Strother et al. | |
| 8,847,548 B2 * | 9/2014 | Kesler | H01F 38/14 |
| | | | 320/108 |
| 8,957,549 B2 * | 2/2015 | Kesler | H03H 7/40 |
| | | | 307/104 |
| 9,812,875 B2 | 11/2017 | Nejatali et al. | |
| 2013/0154373 A1 * | 6/2013 | Lisuwandi | H02J 50/12 |
| | | | 307/34 |
| 2015/0012061 A1 | 1/2015 | Chen | |
| 2017/0098962 A1 * | 4/2017 | Desrosiers | H02M 3/158 |
| 2017/0118722 A1 * | 4/2017 | Hong | H02J 50/12 |
| 2018/0083473 A1 * | 3/2018 | Menegoli | H02J 7/00712 |
| 2018/0337547 A1 * | 11/2018 | Menegoli | H02J 7/0027 |
| 2018/0367187 A1 * | 12/2018 | McFarthing | H04B 5/0031 |
| 2020/0144846 A1 * | 5/2020 | Shin | H02J 50/80 |

OTHER PUBLICATIONS

Pflug, H. et al., "Parallel Resonant Inductive Wireless Power Transfer," Proceedings of Wireless Power Week 2019, Jun. 17, 2019, London, United Kingdom, 5 pages.

* cited by examiner

WIRELESS POWER TRANSFER FOR MEDICAL DEVICES

CROSS-REFERENCE TO RELATED APPLICATION

The present application claims priority to German Provisional Patent Application No. 10 2019 000 915.0, entitled "PARALLEL RESONANT INDUCTIVE WIRELESS POWER TRANSFER", and filed on Feb. 9, 2019. The entire contents of the above-listed application is hereby incorporated by reference for all purposes.

FIELD

The disclosure relates to systems and methods for wireless power transfer for medical devices, such as implantable medical devices.

BACKGROUND AND SUMMARY

An Implantable Medical Device (IMD) may be, e.g., an implantable pulse generating system, such as a neurostimulator. In recent years, both medical devices for spinal cord stimulation (SCS) and wireless power transfer (WPT) systems have seen major innovative improvements, providing increasing possibilities for patient treatment. Parallel resonant inductive wireless power transfer systems for medical implant applications are discussed herein, which may charge transcutaneously an SCS implantable pulse generator (IPG) for patients suffering from a spinal cord injury (SCI).

Pulse generating systems may be used in various medical applications, inter alia from pacemakers and neuromodulation applications, such as neuromodulation for the treatment of a subject, e.g., in the field of improving recovery after neurological disorders such as spinal cord injury and/or stroke. Pulse generation systems may be implantable and may be used to deliver adaptive electrical spinal cord stimulation to facilitate and restore locomotion after neuromotor impairment.

Communication and power charging systems in medical fields may be used to submit energy and communication signals transcutaneously, such as between a non-implanted device and an IPG.

However, in an inductive wireless power transfer link, the transferred current, e.g., for charging an IPG battery, may vary by more than a factor 2 or 3, if the charging distance is varying within a range of 10 millimeters (mm) to 20 mm. The resulting more severe loading of the battery may reduce the capacity and lifetime of the battery. It may also lead to increased thermal heating, due to an increase in average dissipation in both the charger and IPG.

Also, inductive wireless power transfer links may not be designed for power efficient operation over a varying charge distance. Some systems might only work (power) efficiently in a range of approximately 10 mm to 20 mm. For these systems, large distance variation may result in a large variation of load impedance at the transmitting output stage, thus leading to a highly inconsistent efficiency due to mismatched impedances. This may result in additional thermal heating due to dissipation, which is a highly adverse effect for an implanted medical device.

Disclosed herein are improved wireless power transfer systems for medical devices, which may advantageously facilitate a highly consistent transfer and may avoid the above-mentioned deficiencies. The transcutaneous charging systems may address a larger range of implant depth compared to other technology, which can, e.g., address a larger population of wheelchair bounded SCI patients.

In a variety of embodiments, a wireless power transfer system for a medical device, such as an 1 MB, may comprise a transmitter unit and a receiver unit. The wireless power transfer system may be configured for transferring power and/or signals from the transmitter unit to the receiver unit and/or vice versa. The transmitter unit may comprise an energy source, a transmitter antenna, and a supply line connected in between the energy source and the antenna. The receiver unit may comprise a receiver antenna and a rectifier output. The transmitter antenna and the receiver antenna may be configured to provide a wireless power transfer link, and the supply line may comprise a virtual resistance unit, which may be configured to provide a virtual resistance.

In some embodiments, wireless power transfer systems may be configured to provide parallel and/or series resonant inductive wireless power transfer from the transmitter unit to the receiver unit. This may advantageously facilitate a very efficient power transfer.

For some embodiments, the virtual resistance unit may be configured to provide a non-linear resistance in the supply line. Thus, the system may advantageously offer wide possibilities for adjusting transfer conditions.

Also, in some embodiments, the supply line may comprise a DC-DC buck/boost-converter unit and a transmit amplifier unit, wherein the virtual resistance unit may be connected to the supply line in between the DC-DC buck/boost-converter unit and the transmit amplifier unit. The transfer conditions may thus advantageously be very finely controlled on the side of the transmitter device.

Using a non-linear virtual resistance in the supply line, such as one arranged between the DC-DC buck/boost-converter and the transmit amplifier, may advantageously facilitate keeping a constant current within an implanted device or reduce a current variation, even when a distance between transmitter and receiver coils is varied. In some embodiments, the virtual resistance may control an inductive output signal that is transmitted from the transmitter unit to the receiver unit.

For some embodiments, the receiver unit may be configured to provide a charger current for charging a battery through the rectifier output. The system may therefore advantageously be used for charging a battery of an implanted device.

In some embodiments, the wireless power transfer system may further be configured to provide a charging current in the range of approximately 50 milliamperes (mA) to 150 mA, such as approximately 100 mA. Thus, the system may advantageously provide optimum charging conditions for an IMD battery.

For some embodiments, a distance between the transmitter antenna and the receiver antenna may be within a predetermined distance range. Thus, the transfer conditions may advantageously be kept within predefined boundaries.

In some embodiments, a distance between the transmitter antenna and the receiver antenna may be within a range of approximately 10 mm to 50 mm. The system may therefore be advantageously useable in a typical distance range, which may cover distance variations due to patient activities or due to the requirements of medical practice.

Also, the virtual resistance may be determined such that the rectifier output provides a substantially constant current, or a reduction in current variation, over the predetermined distance range, e.g., a substantially constant charging current of approximately 100 mA. Thus, the system may advantageously provide consistently optimum or improved conditions for charging the IMD battery under typical conditions of medical applications.

Also disclosed herein are methods for performing improved wireless power transfer for medical devices. In a variety of embodiments, a method of performing wireless power transfer for a medical device, such as an IMD, by transferring power from a transmitter unit to a receiver unit may comprise various steps. A charger current may be provided from an energy source through a supply line to a transmitter antenna of the transmitter unit. A virtual resistance may be provided by a virtual resistance unit in the supply line. A modulated magnetic field may be generated through the transmitter antenna. The modulated magnetic field may be received through a receiver antenna of the receiver unit. A charging current may then be generated in the receiver unit. The methods may be configured for the operation of the systems disclosed herein. Thus, the same advantages that apply to the systems may apply to the methods.

In some embodiments, a modulated magnetic field may be generated such that a parallel resonant inductive wireless power transfer may be performed. Various such methods may be performed by means of the systems disclosed herein.

Some embodiments may use wireless power transfer systems for charging a battery of an IMD. For example, the system may be used for charging the battery of an IPG system.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The disclosure may be better understood from reading the following description of non-limiting embodiments, with reference to the attached drawings, wherein below.

DETAILED DESCRIPTION

Figure 1:
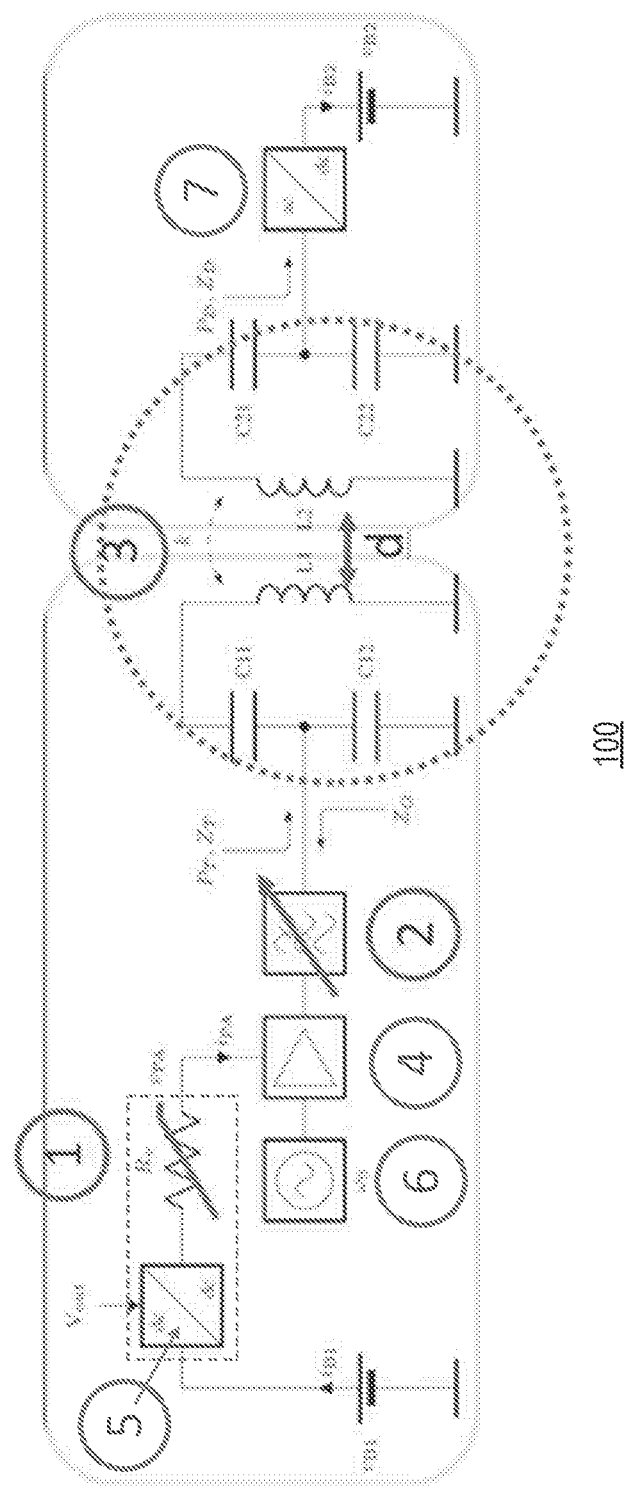
FIG. 1 shows a wireless power transfer system in accordance with one or more embodiments of the present disclosure.

The systems and methods disclosed herein are based on the basic idea that, by adjusting a virtual resistance in a supply line, the systems may advantageously facilitate providing a consistent power transfer and, e.g., a constant or less varying current in an IMD. By this, a large range of implant depth can be achieved, and a constant or less varying charge current into an IMD battery can be obtained even over varying charge distances. In tests, charging distances of more than 50 mm have been obtained.

By controlling the charging signal in a charging coil of the transmitter device, a constant or less varying charge current can be obtained in the IMD for charging its battery, over varying charging distances between transmitter and receiver coils and antennas, respectively. To that end, the virtual resistance may be controlled by a sensing circuit, which may be configured to sense a voltage or current within the supply line. This control may benefit from monotonic voltage or current variations as a function of the charging distance. This serves to avoid a property of some systems, e.g., a widely varying behavior of currents for charging the battery in the receiver unit, e.g., by a factor of 2, when the charging distance varies within a range of 10 mm to 50 mm, due to a resulting large variation of load impedance.

The systems may advantageously provide constant or less varying charging current for the IMD battery, even when the transmitter and receiver units move relatively to each other. Such movements may be caused by, e.g., patient interactions or other activities of the patient, for example breathing.

Furthermore, thermal heating due to a non-linear relationship between dissipation and battery current may be advantageously reduced. In some systems, such thermal heating presents a severe design challenge. The systems may help to overcome this problem.

Also, the systems may eliminate a need for a wireless feedback loop from the IMD to the charger device to control the charging current to the battery, which may have a slow update rate, e.g., every 10 seconds, and thus allows only slow reactions.

Furthermore, the systems may enable an easier fault condition signaling in the IMD, when the charging current is clearly different from a predetermined, intended value.

To implement the systems, the supply line of a transmitter unit, which may be configured as a charger device, may comprise a DC-DC converter circuit, which makes a current monitor output available, such as by means of an output pin. This output signal may be captured by an analog-digital converter circuit (ADC), e.g., comprised by a microcontroller, which may also be available in the transmitter unit. For example, a look-up-table may be used to convert a measured current value into a corresponding required voltage, e.g., through a converging successive approximation type of algorithm.

In the disclosed systems, an amplifier output filter/matching circuit of the transmitter unit may be optimized for minimizing thermal heating due to dissipation, e.g., by using a load pull simulation/measurement technique, as may be used in the field of amplifier design. Thus, the efficiency of the wireless power transfer process may be increased. Also, a sufficient IMD battery current may be reached even at a large distance, e.g., up to a distance of 50 mm. The resulting values may be verified by a measurement of efficiency and transferred current under laboratory conditions.

By optimizing the ratios of capacitors in the parallel resonant wireless power transfer circuit in the transmitter and receiver unit, respectively, thermal heating due to dissipation may be minimized. Also, a sufficient IMD battery charging current may be reached, e.g., at a distance of 50 mm.

Furthermore, the oscillation frequency of the transmitter unit, which may be configured as a charger device, and/or a duty-cycle of amplifier and/or matching filter characteristics, may be adapted such that the charging current provided to the IMD battery is regulated to automatically reach a desired level of, e.g., 100 mA, or to keep it within a desired range of, e.g., 75 mA to 125 mA.

Also, non-linear resistance characteristics may be used for multiple charge current levels. Thus, constant voltage charging of the battery may be emulated by selecting the non-linear resistance characteristics based on the desired charge current to emulate constant voltage charging.

The non-linear virtual resistance characteristics, as defined by a voltage-current relation, may be configured for a delivery of a constant or less varying IMD battery charging current. Alternatively, it can be partially exchanged against a higher charger efficiency and/or charger power dissipation, resulting in less thermal heating, as discussed above.

Referring to FIG. 1, a WPT system 100 according to some embodiments, related to a transcutaneous parallel resonant WPT circuit diagram, is explained. The system may be configured for transcutaneous charging a battery of an IMD, such as an IPG system.

The system may comprise a transmitter unit, such as a charger device (the left-hand box) with a first inductive element L1 (e.g., a charging coil). It may further comprise a receiver unit (the right-hand box) with a second inductive element L2 and a rectifier circuit 7.

The transmitter and receiver unit may be arranged at a distance d; accordingly, distance d may denote a distance between first inductive element L1 and second inductive element L2. In some embodiments, a 6.78 megahertz (MHz) Industrial/Scientific/Medical (ISM) band signal frequency may be used (e.g., in an oscillator 6 of the transmitter unit).

The transmitter device may comprise an energy source providing a voltage $v_{B1}$ to a supply line. In the supply line, a DC-DC converter 5 (which may comprise a DC-DC buck/boost converter) may be arranged. Furthermore, the supply line may comprise a virtual resistance unit 1 (which may be tunable). Rectifier circuit 7 of the receiver unit (which may comprise an AC-DC converter) may rectify or convert an incoming alternating-current voltage (and/or current) to a direct-current voltage (and/or current). An output of the rectifier circuit 7 (such as a voltage output and/or current output) may then provide a charging current for charging the battery of the IMD.

Virtual resistance unit 1 may be arranged in the supply line between the DC-DC buck/boost-converter and a transmit amplifier 4 (which may comprise, e.g., a class-D amplifier, by which a voltage $v_{P4}$ and/or current $i_{P4}$ for the inductive output charging signal in inductive element L1 is controlled. In some embodiments, DC-DC converter 5 may incorporate virtual resistance unit 1, or circuitry may be added to allow DC-DC converter 5 to behave as if a resistance (e.g., the virtual resistance) is present in the supply line (as depicted by the dashed line around DC-DC converter 5 and virtual resistance unit 1). Virtual resistance unit 1 may be configured such that a constant or less varying charge current $i_{B2}$ into the IPG battery $v_{B2}$ is obtained over a varying charge distance d between L1 and L2, which together may provide an inductively coupled (parallel) resonant circuitry 3.

In some embodiments, the virtual resistance of virtual resistance unit 1 may be controlled by a voltage $v_{P4}$ or current $i_{P4}$ sensing circuit. This control may work best for monotonic voltage or current variation versus variation of distance d. Normally, a large $i_{B2}$ variation occurs of more than, e.g., a factor 2 or 3 when the distance d is varied between 10 mm and 50 mm, due to a resulting large load impedance $Z_T$ variation.

Some embodiments may be configured such that an amplifier output filter/matching circuit 2 (which may be tunable) is optimized for minimizing thermal heating due to dissipation. Embodiments may be further configured such that a sufficient IMD battery current $i_{B2}$ is obtained at 50 mm distance d. Thus, an increased efficiency is reached.

In various embodiments, the transmitter device and receiver device may comprise capacitors C11, C12 and C21, C22, respectively. In some embodiments, the ratios of capacitance of C11/C12 and C21/C22 may be chosen depending on each other, to minimize thermal heating due to dissipation and to obtain sufficient $i_{B2}$ IMD battery current at the outer distance ranges d of, e.g., 10 mm to 50 mm.

Furthermore, the system may be configured such that the output oscillation frequency of oscillator 6, the duty-cycle of amplifier 4 and/or characteristics of matching filter 2 are chosen to automatically regulate the charging current to the desired level of, e.g., 100 mA, or to keep it within the desired range of, e.g., 75 mA to 125 mA.

Specific resistance characteristics may be selectable for multiple charge current levels: When WPT is performed, a resistance characteristic may be selected based on the desired charge current, for example, to emulate constant voltage charging of the battery. According to some embodiments, the virtual resistance characteristics may be defined by a voltage-current relation, which may provide a constant or less varying delivery of IDM battery charging current. In various embodiments, virtual resistance unit 1 may be a non-linear virtual resistance unit, and may have a voltage-current relation that defines non-linear virtual resistance characteristics. Accordingly, non-linear resistance characteristics may be selectable based on a desired charge current, to emulate constant voltage charging of the battery.

Also, the characteristics may be partially optimized for higher charger efficiency and/or with regards to charger power dissipation, resulting in less thermal heating.

Accordingly, in various embodiments, a virtual resistance unit may provide a resistance in a supply line in a transmitter unit as disclosed herein. The resistance provided by the virtual resistance unit may implicitly establish the supply line voltage $v_{P4}$ and/or supply line current $i_{P4}$. The resistance may be realized and/or controlled by a sensing circuit. For example, a DC-DC converter circuit may have an internal current sense amplifier sensing the supply line current $i_{P4}$ the converter delivers to the supply line while the converter's output voltage, the supply line voltage $v_{P4}$, can be sensed through a (separate) resistive divider. The output of the current sense amplifier and/or resistive divider may be made available, and a digitized version of these signals may be presented to a look-up table to convert a measured current value $i_{P4}$ and/or voltage value $v_{P4}$ into a corresponding control signal $v_{OUT}$ of the DC-DC converter setting its output voltage $v_{P4}$ that will ultimately, through the interaction between inductive elements L1 and L2, establish a constant or less varying charging current for the IMD battery, for example, caused by variations in distance d or spread in component values from one WPT system to the other. The controlled (output) voltage $v_{P4}$ may be a function of, among other factors, a distance d between L1 and L2.

Thus, the sensing and control circuit may: (1) monitor a current and/or output voltage of the DC-DC converter circuit and/or the supply line; (2) determine the voltage $v_{P4}$ and/or current $i_{P4}$ that may cause a desired constant or less varying charging current, given the (implicitly derived) distance d (for example, by consulting a lookup table); and (3) control a resistance of the virtual resistance unit by controlling the DC-DC converter's output voltage so that the resistance provided by the virtual resistance unit will establish the voltage $v_{P4}$ and/or current $i_{P4}$ necessary to cause the desired constant or less varying charging current for the IMD battery. The distance d may be accounted for via one or more parameters available to the transmitter unit. For example, in accounting for the distance d, the system may make use of transmitter current and/or voltage information, such as the $i_{P4}$ supply line current or supply line voltage $v_{P4}$, or an RF voltage amplitude (which may be available from the output filter/matching circuitry). If one of the signals does not provide a fully monotonic response, a combination of two or more signals could provide a monotonic relation to distance d.

Referring to FIGS. 2 to 9, a WPT system according to some embodiments is explained, together with reference and simulation results. For some embodiments, a target transferred current of 100 mA is assumed over an implant depth of 10 mm to 50 mm. Hereinafter, parallel resonant L-C tank circuits will be analyzed, which may form the heart of a WPT system. Afterwards, methods will be discussed for proper rectifier comparison, resulting in advantageous topologies for this application. Furthermore, insight will be given in the transmitter class-D amplifier matching and modeling, and a resulting transcutaneous charging system performance will be shown.

Radiative wireless power transfer efficiency may be very low as the radiation is typically omnidirectional. Non-radiative magnetic power transfer may be a good alternative, however, the usual non-resonant induction may be very inefficient for midrange applications. Efficient midrange power transfer is possible with magnetic resonant objects strongly coupled to one another, like inductors (Kurs et al., "Wireless Power Transfer via Strongly Coupled Magnetic Resonances", Science, vol. 317, no. 5834, pp. 83-86, 2007). For some embodiments, inductor quality factors Q may be in a range of about 50-70, meaning some such embodiments may take place in a strongly coupled regime (kQ in a range of about 1-10 with k being the inductor coupling factor), which is similar to Kurs et al. describing larger distances due to higher quality factor and larger size inductors.

WPT systems may be designed for a fixed transmitter to receiver distance. The implant use case has to cope with a variable distance. For a transmitter to receiver distance range of 10 mm to 50 mm, an inductor coupling factor k may vary between 0.2 and 0.02. Such a range may result in a large impedance variation across the coupled section, as will be shown later.

The coils may form a resonating circuit at 6.78 MHz, for example, which can be either a series and/or parallel configuration. When a load impedance on the secondary side is higher than an impedance of the receiver coil at the resonance frequency, parallel resonance may be best to be used on that side. A large load on a series resonant circuit may damp a secondary tank resonance too much (van Schuylenbergh et al., Inductive Powering: Basic Theory and Application to Biomedical Systems, ser. Analog Circuits and Signal Processing. Springer Netherlands, 2009).

For the primary side both options can be interchanged (Ni et al., "Design and Comparison of Parallel and Series Resonant Topology in Wireless Power Transfer," in 2013 IEEE 8th Conference on Industrial Electronics and Applications (ICIEA), June 2013, pp. 1832-1837). In order to provide more design freedom on the primary side some designs may provide a parallel resonance. For medical implanted devices, dissipation may be kept to a minimum. Therefore, the system may be designed not merely for transferred current but also for minimal dissipation.

Figure 2:
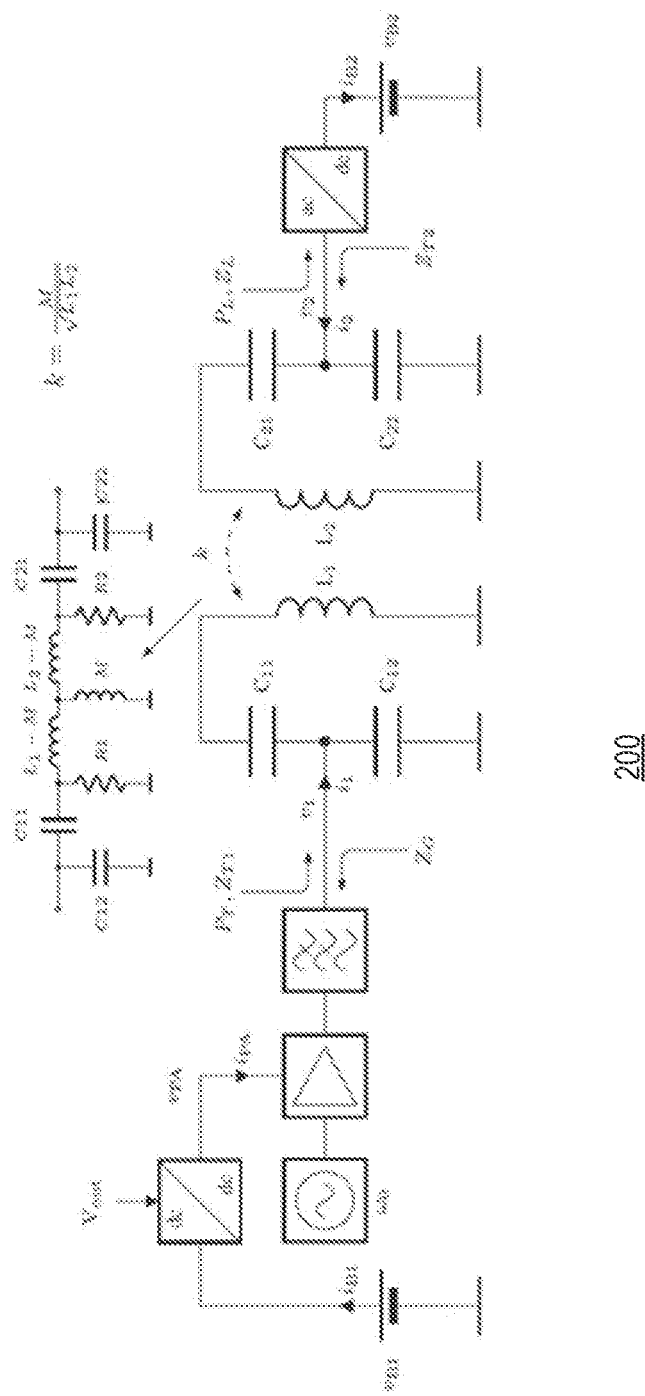
FIG. 2 shows a wireless power transfer system in accordance with one or more embodiments of the present disclosure.

A first example is a transcutaneous parallel resonant WPT circuit diagram, which is shown in FIG. 2. FIG. 2 illustrates a parallel resonant WPT circuit 200. The circuit may comprise tapped-C transformers. An equivalent coupled inductor circuit is shown on top.

In FIG. 2, voltages $v_1$ and $v_2$ may be defined (with respect to ground) as the wireless transfer network input and output voltages, with corresponding currents $i_1$ and $i_2$ also shown. The circuitry generating the transmit signal (left of $v_1$) may be represented as a sinusoidal voltage source with amplitude $V_G$ and output resistance $Z_G$. The network may be loaded with a rectifier circuit (AC-DC converter) and a rechargeable battery. These are modeled as a fixed load impedance $Z_L$d.

The wireless transfer network may be a reciprocal two-port network (e.g. $Z_{21}=Z_{12}$), represented by its impedance matrix, with elements $Z_{ij}=R_{ij}+jX_{ij}$, with i, j=1, 2, given the realization of the wireless power transfer link in accordance with equation 1 below.

$$\begin{pmatrix} v_1 \\ v_2 \end{pmatrix} = \begin{pmatrix} Z_{1,1} & Z_{1,2} \\ Z_{2,1} & Z_{2,2} \end{pmatrix} \begin{pmatrix} i_1 \\ i_2 \end{pmatrix} \qquad (1)$$

Using linear network theory, the wireless transfer equation may be derived for $i_2$ in accordance with equation 2 below:

$$i_2 = \frac{V_G Z_{2,1}}{(Z_{2,2}+Z_L)(Z_{1,1}+Z_G) - Z_{2,1}^2} \qquad (2)$$

Figure 3:
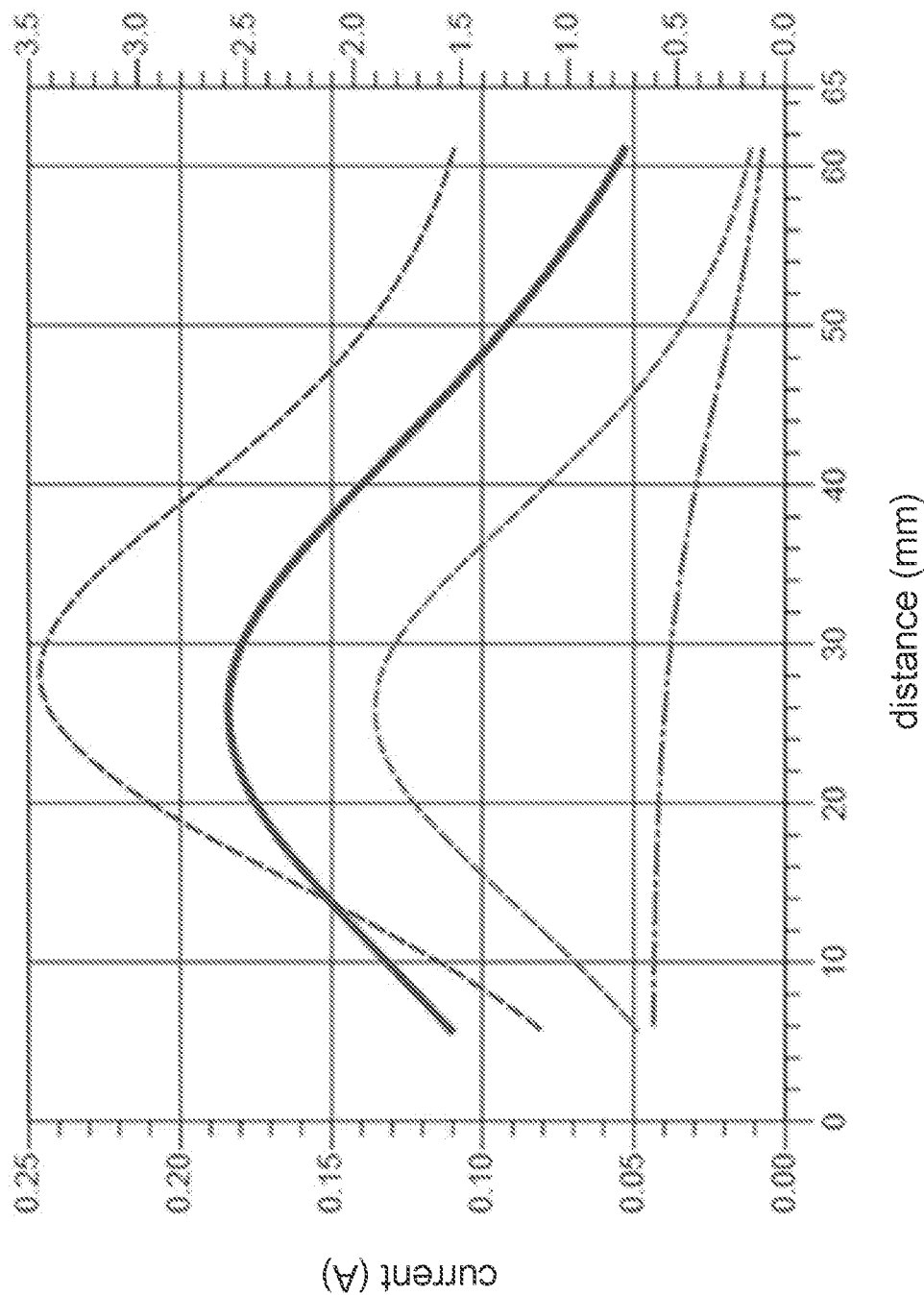
FIG. 3 shows a graph of WPT transferred current versus distance according to at least one example of the present disclosure.

Typical values used for these elements are shown in Table 1 and the resulting transferred current $i_2$ and power $P_T$ and $P_L$ with their efficiency ratio in FIG. 3.

In FIG. 3, a graph 300 shows resonant WPT transferred current $i_2$ (the solid line), input power $P_T$ (the upper dashed line), and output power $P_L$ (the lower dashed line) corresponding to FIG. 2 and Table 1. Also shown is the transfer efficiency $\eta T=P_L/P_T$ (the dotted-and-dashed line). Power may be calculated using $P_T=\Re(v_1 i_1^*)$ and $P_L=\Re(v_2 i_2^*)$ for the inductors used, with k being related to distance in accordance with equation 3:

$$d=-42.53\log_{10}(k)-24.0(mm) \qquad (3)$$

TABLE 1

Typical values used, with $R_1$ and $R_2$ representing resonator loss

| | |
|---|---|
| $V_G$: | 47 V |
| $Z_G$: | 80 Ω |
| $C_{12}$: | 880 pF |
| $C_{11}$: | 220 pF |
| $R_1$: | 17.4 kΩ |

TABLE 1-continued

Typical values used, with $R_1$ and $R_2$ representing resonator loss

| | |
|---|---|
| $L_1$: | 3.1 µH |
| M: | 20-600 nH |
| $L_2$: | 2.8 µH |
| $R_2$: | 4.74 kΩ |
| $C_{21}$: | 245 pF |
| $C_{22}$: | 1000 pF |
| $Z_L$: | 112 + j7 Ω |

Figure 4:
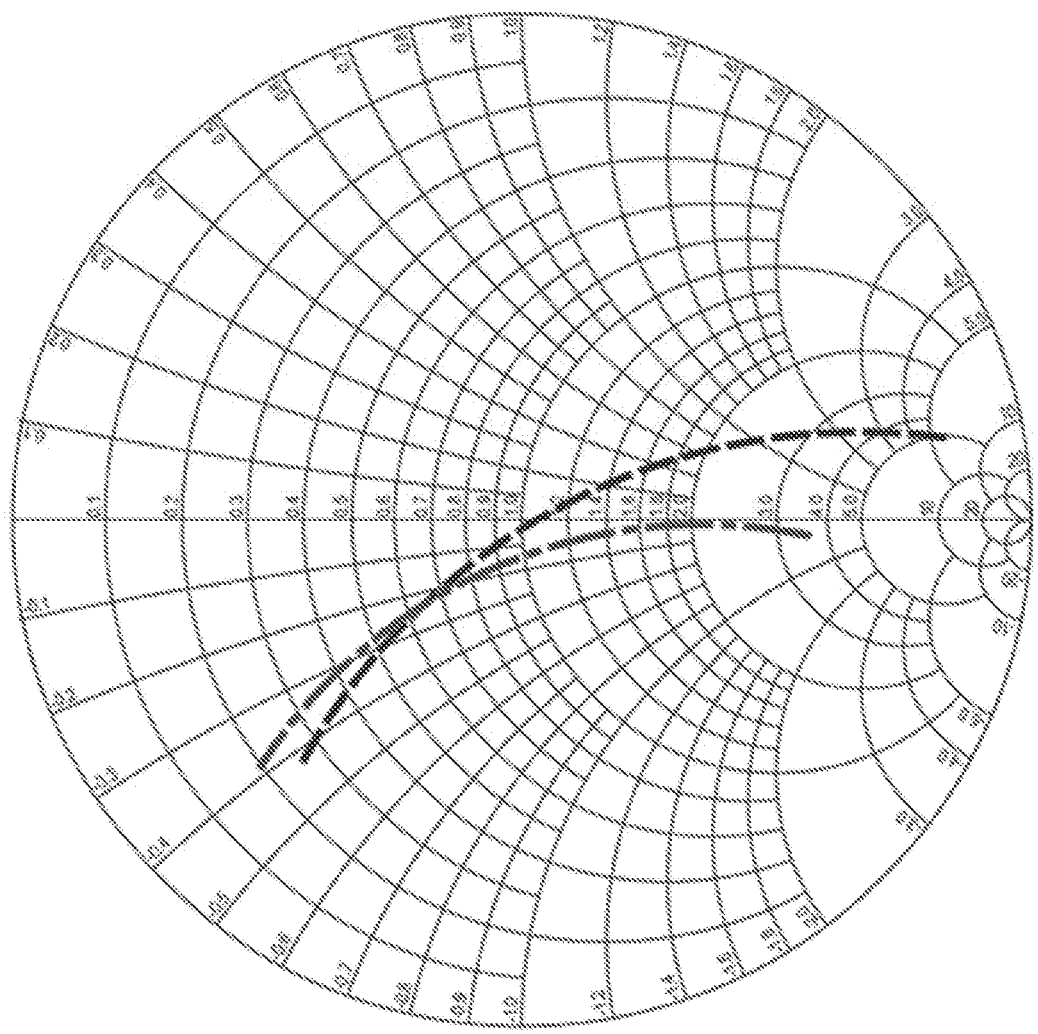
FIG. 4 shows a Smith chart for impedances according to at least one example of the present disclosure.

As will be discussed later, the variation along distance of $i_2$, $P_T$ and $P_L$ may be due to a wide variation in source load impedance $Z_{T1}$ (see FIG. 4), resulting in reflected energy and a non-optimal power transfer into the resonating circuit. In FIG. 4, calculated $Z_{T1}$ (the dashed line) and $Z_{T2}$ (the dotted-and-dashed line) are shown on a Smith chart 400 where impedances are converted and normalized to 50Ω reference. Both curves move from left (d=5.7 mm) to right (d=61 mm). The transfer efficiency $\eta=P_L/P_T$ is a monotonic decreasing function for increasing distance, due to the reducing in $L_2$ flux. $R_2$, representing the right resonator loss, accounts for 85% of η (no loss in primary resonator, only reflection at input depending on distance/impedance), $R_1$ (left resonator loss) accounts for 99% at d=5 mm to 48% at d=50 mm.

Selecting the most optimal rectifier topology for a WPT system may employ a method to compare circuits all operating at a specific and same operating point. In this work, a required battery charge current may be the target system design parameter. This may set a specific rectifier dc-output power. The corresponding rectifier input impedance $Z_L$ and power $P_L$ can be calculated (simulated) from the rectifier input voltage $v_L$ and current $i_L$ as shown in FIG. 5.

Figure 5:
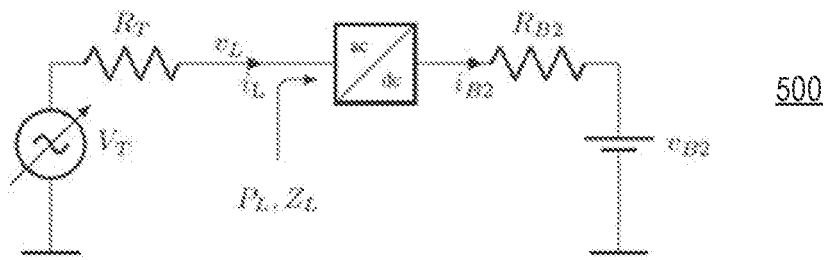
FIG. 5 shows a circuit for obtaining a rectifier input impedance according to at least one example of the present disclosure.

FIG. 5 shows a concept 500 to obtain rectifier input impedance and efficiency at specified output current using Advanced Design System (ADS) simulation software. The method used to compare different rectifier topologies is to tune the source voltage amplitude $V_G$ to obtain a specified battery charge current $i_{B2}$. Next to efficiency and input impedance, other aspects can also be used for selection like e.g. component count and -size.

It is noted that, as this is a non-linear circuit, with typically significant circuit input voltage, the shape of the diode voltage is not equal to the voltage waveform generated at the source used in the analysis (typically a sinusoidal waveform) and dependent on the source output impedance. Using an average value for the range of occurring impedance, is found to be sufficiently accurate in the case of a WPT system using a source output power of a few Watts.

In this embodiment, a balanced rectifier circuit is used. Two configurations are found to have highest efficiency figures, a double Schottky-diode combined with two inductors type, named push-push rectifier (see FIG. 6) and the well known full-bridge rectifier consisting of four Schottky diodes.

Figure 6:
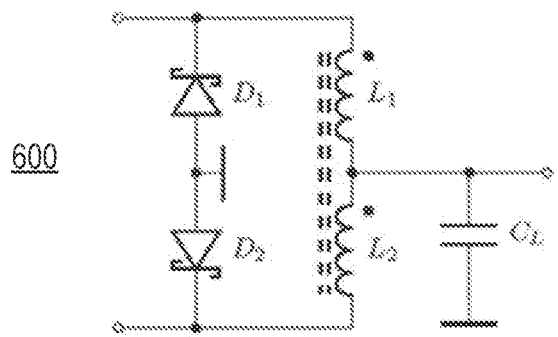
FIG. 6 shows a topology for a balanced-in, single ended-out push-push rectifier according to at least one example of the present disclosure.

FIG. 6 shows a balanced-in, single ended-out push-push rectifier topology 600 with coupled inductors; diodes and inductors can swap place. Using the comparison concept described above, the two topologies are compared for different source resistance values (Table 2) and for the expected range of battery voltages (Table 3). This shows that both variations have an impact on both rectifier input impedance and efficiency. It also shows that the push-push type has higher impedance and less variation over battery voltage. Varying the required charging current shows that the impedance increases significantly when lowering the current, and the efficiency goes up slightly. A variant on the push-push topology, with uncoupled inductors, has even higher efficiency but is not chosen for printed circuit board space reasons.

TABLE 2

Simulated push-push and full-bridge rectifier performance as a function of the source output impedance, optimized for $i_{B2}$ = 100 mA into a 4.2 V battery:

| | Push-push | | | Full bridge | |
|---|---|---|---|---|---|
| $R_T$ (Ω) | $Z_D$ (Ω) | η (%) | | $Z_D$ (Ω) | η (%) |
| 10 | 113.8 + j8.3 | 87.7 | | 31.9 − j1.1 | 86.6 |
| 50 | 125.3 + j9.1 | 89.9 | | 36.0 − j2.4 | 87.5 |
| 200 | 138.5 + j6.9 | 91.7 | | 38.0 − j5.1 | 87.8 |
| 400 | 144.0 + j2.1 | 91.7 | | 38.4 − j5.5 | 87.8 |

TABLE 3

Simulated rectifier performance against battery voltage, optimized for $i_{B2}$ = 100 mA at $R_T$ = 50 Ω:

| | Push-push | | | Full bridge | |
|---|---|---|---|---|---|
| $V_{B2}$ (V) | $Z_D$ (Ω) | $η^a$ (%) | | $Z_D$ (Ω) | η (%) |
| 3.0 | 96.5 + j4.6 | 87.2 | | 27.8 − j1.8 | 83.7 |
| 3.4 | 106.2 + j5.4 | 88.3 | | 30.6 − j2.0 | 85.2 |
| 3.8 | 115.8 + j7.4 | 89.2 | | 33.3 − j2.2 | 86.4 |
| 4.2 | 125.3 + j9.1 | 89.9 | | 36.0 − j2.4 | 87.5 |

[a]common mode coil resistance is modeled as $R_L$ = 0.6 Ω for dc and RL = 2.5 Ω for RF frequencies.

For the amplification of the generated charge signal, a class-D amplifier is a useful topology to use, as it is efficient and can cope with a large load impedance variation (Schuylenbergh et al.). Class-D amplifiers have been used for more than five decades (Page et al., "On Solid-State Class-D Systems," Proceedings of the IEEE, vol. 53, no. 4, pp. 423-424, April 1965; Chudobiak et al., "Frequency and Power Limitations of Class-D Transistor Amplifiers," IEEE Journal of Solid-State Circuits, vol. 4, no. 1, pp. 25-37, February 1969).

A class-D amplifier consists, e.g., of two MOSFET's. The available models do not provide easy convergence in a frequency domain simulation like ADS Harmonic Balance. In the time domain, a simulation using these models takes time. For this reason a simplified model is used based on switches, see FIG. 7.

Figure 7:
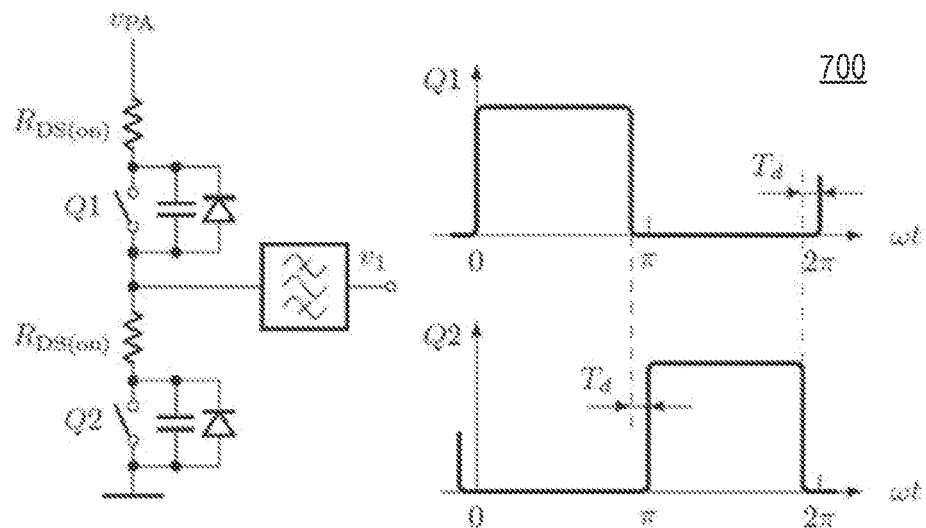
FIG. 7 shows a Class-D amplifier model according to at least one example of the present disclosure.

FIG. 7 shows a Class-D amplifier model 700 used in this work, consisting of (on the left) two switching MOSFETs, modeled as ideal switch with RDS(on) resistance, a body diode and drain-source capacitance. The timing diagram of the switches is shown on the right, with an indication of the dead time $T_d$=5%. In a time domain simulation both models are compared and found providing sufficiently equal output signals at a class-D amplifier example operating at 6.78 MHz. The switch-based class-D model does simulate well in frequency domain and enables more complex types of analysis like load pull with even including component tuning.

For the present embodiment, a quasi-complementary (both N-type) voltage switching push-pull class-D power amplifier is used (Krauss et al., Solid State Radio Engineering. John Wiley & Sons, Inc., 1980; Grebennikov et al., Switchmode RF and Microwave Power Amplifiers, Second Edition, 2nd ed. Orlando, Fla., USA: Academic Press, Inc., 2012). For this configuration, the output filter is typically of the series L-C-R type (inductor, capacitor, resistor) where the load is formed by the resistor. The calculation of the load resistor as a function of supply voltage and required output power (Krauss et al.) may be done in accordance with equation 4 below:

$$P_T = \frac{2v_{PA}^2}{\pi^2 R_{T1}} \quad (4)$$

where $R_{T1}=\Re(Z_{T1})$ (see FIG. 2). From FIG. 3 and Tables 2 and 3, it follows that approximately $P_T=1.5$ Watt is required, resulting in $R_{T1}=13.5\Omega$ for $v_{PA}=10$ V. Equation 4 provides the relation between $P_T$, $v_{PA}$ and $R_T$. Using a load pull analysis it shows that this resistance does not correspond to the load impedance for optimal delivered output power, which is also clear from equation 4. It is more a good compromise between efficiency and delivered output power.

Modifying to class-D output filter to a series-L, parallel C-R configuration has the advantage that for the same output power, the matching load impedance has a higher value. Equations 5a, 5b, and 5c below can be used (Bowick, RF Circuit Design, ser. Electronics & Electrical. Newnes, 1997):

$$Q_s = \frac{1}{\omega C_s R_s} \quad (5a)$$

$$R_p = (Q_s^2 + 1)R_s \quad (5b)$$

$$X_p = R_p / Q_p \quad (5c)$$

where $Q_s$ is the series quality factor, $X_p$ the capacitor reactance and $Q_p=Q_s$. The higher load impedance matches better with the observed range of values expected in the foreseen WPT system (FIG. 4), resulting in a higher efficient system.

Figure 8:
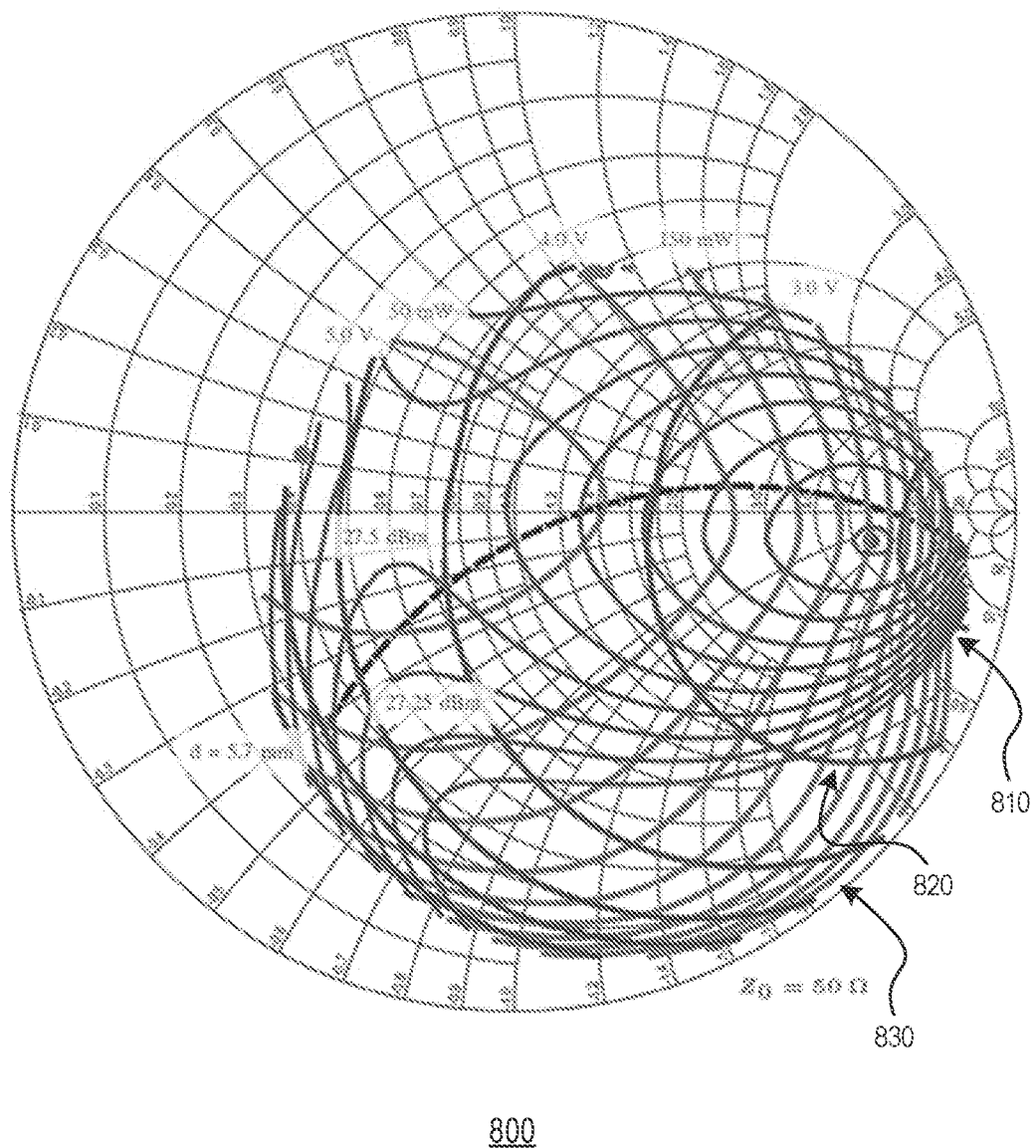
FIG. 8 shows a Smith chart for a load pull simulation result according to at least one example of the present disclosure.

FIG. 8 shows a Smith chart 800 for an ADS load pull simulation result, showing class-D amplifier optimal load impedance for a delivered power $P_T$ 810, an amplifier supply voltage $v_{PA}$ 820 and an amplifier dissipation $P_{diss}$ 830 for a constant rectifier input power level of $P_L=30$ dBm. Also shown is the amplifier load impedance, for d=5.7 mm (left) to d=61.1 mm (right) (dashed). Based on 4096 simulated reflection coefficients using ADS circuit model (FIG. 7), with $v_{PA,min}=1.7$ Vat $Z_T=546-j430\Omega$, $P_{T,opt}=29.0$ dBm at $Z_T=283-j66.7\Omega$, and $P_{diss,min}=16$ mW at $Z_T=19.8+j5.7\Omega$ The $v_{PA,min}$-step size is 1 V, the $P_T$ step size is 0.25 dB, and the dissipation step size is 50 mW.

For the results shown in FIG. 8, a load pull simulation was carried out of the class-D amplifier with series-L (330 nH), parallel-C (1660 pF) output filter. This configuration may be optimized for optimal output power at large coil distance, as can be seen from the graph. Dissipation may increase with increasing coil distance. As in the actual use case the system is controlled for constant or less varying charge current, the setup of the simulation is such that $P_L=30$ dBm may be obtained over the range of coil distances. Using the same technique, the system can be further optimized for lowest power dissipation (Liu et al., "A High-Efficiency Class-E Power Amplifier with Wide-Range Load in WPT Systems", in 2015 IEEE Wireless Power Transfer Conference (WPTC), May 2015, pp. 1-3).

Figure 9:
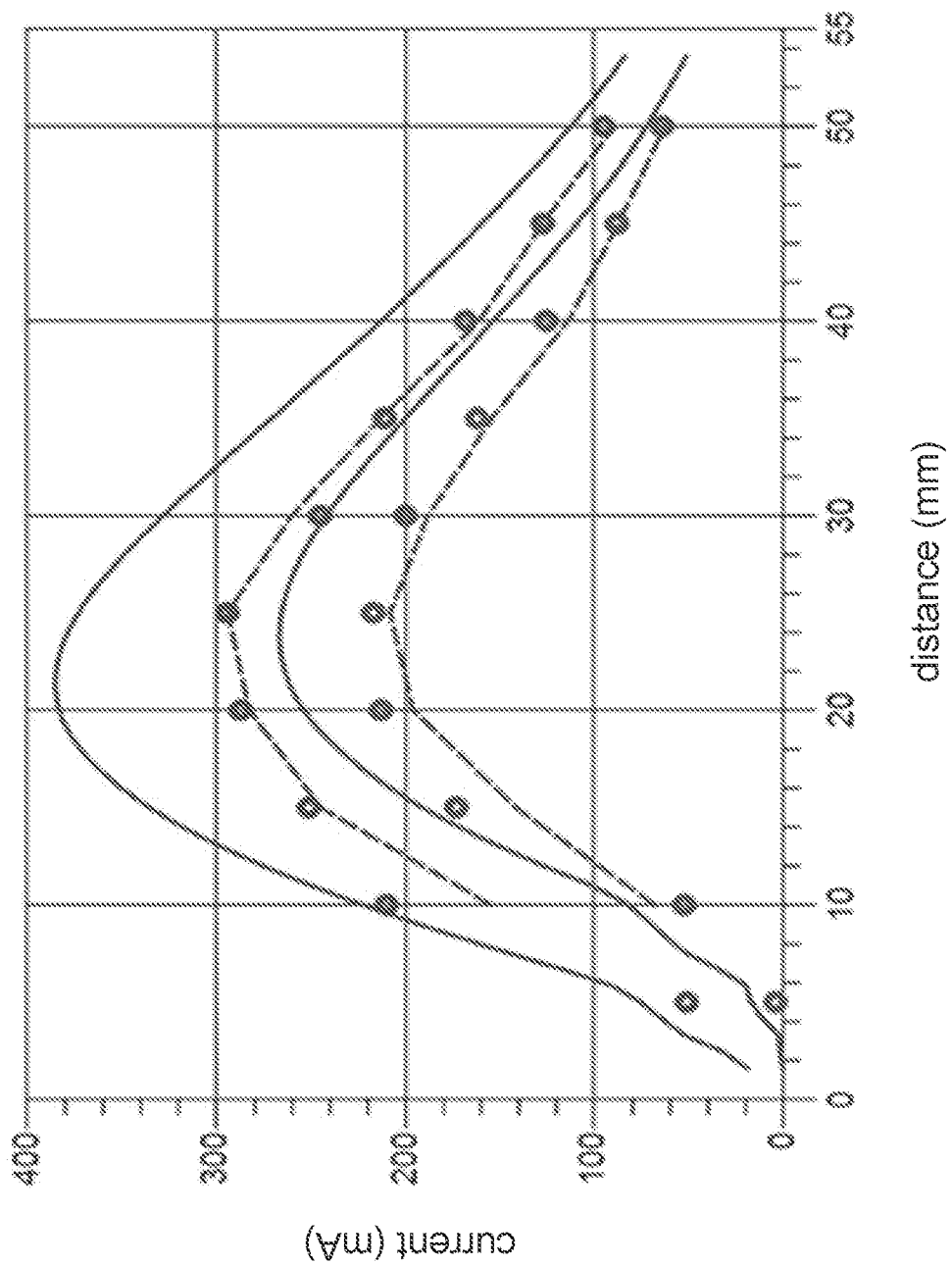
FIG. 9 shows a graph for simulated WPT transferred current versus distance according to at least one example of the present disclosure.

Combining the above elements of the complete WPT system, FIG. 9 shows a graph 900 of a comparison between measured and simulated data of a transcutaneous SCS WPT example, at two different class-D supply voltage levels. FIG. 9 shows a simulated frequency domain (solid lines), time domain (dashed lines) and measured (sets of dots) WPT transferred current $i_{B2}$ corresponding to FIG. 2 and Table 1, for both $v_{PA}=12$ V (upper solid line, dashed line, and set of dots) and 10 V (lower solid line, dashed line, and set of dots). Simulations are done both in the time domain (using an Infineon non-linear MOSFET model) and in the frequency domain (using a simplified model shown in FIG. 7). The time domain simulation takes about 2059 seconds, the frequency domain one 4.8 seconds; a factor 400 faster. The frequency domain model may be less accurate, but may enable a more complex analysis like a load pull simulation as shown in FIG. 8, which required 4096 simulation points. Even sweeping a component value on a load pull simulation is usable, providing useful insight in circuit behavior against component variation. Also, system optimization may be possible in a reasonable amount of time. A final check in the time domain can lead to the final design.

Above, a parallel resonant inductive wireless power transfer system and a systematic analysis of its elements are presented. The concept of a transcutaneous charging system addressing a larger range of implant depth is shown to be possible, both in simulation and measurement. The impact of the large implant depth range on amplifier load impedance and with that, design and modeling, are shown from an analytical standpoint. Together with an objective simulation comparison approach for rectifier topologies to facilitate an efficient design and show that a transferred current of 100 mA measured over an implant depth of 10 mm to 50 mm and fits well both a time-domain and a frequency-domain simulation model. Using the latter enabled complex analyses like class-D amplifier load pull combined with component tuning, due to its factor-of-400 increase in simulation speed. Using this, medical devices may advantageously be designed for minimal dissipation and maximum performance.

The description of embodiments has been presented for purposes of illustration and description. Suitable modifications and variations to the embodiments may be performed in light of the above description or may be acquired from practicing the methods. For example, unless otherwise noted, one or more of the described methods may be performed by a suitable device and/or combination of devices. The methods may be performed by executing stored instructions with one or more logic devices (e.g., processors) in combination with one or more additional hardware elements, such as storage devices, memory, image sensors/lens systems, light sensors, hardware network interfaces/antennas, switches, actuators, clock circuits, and so on. The described methods and associated actions may also be performed in various orders in addition to the order described in this application, in parallel, and/or simultaneously. The described systems are exemplary in nature, and may include additional elements and/or omit elements. The subject matter of the present disclosure includes all novel and non-obvious combinations and sub-combinations of the various systems and configurations, and other features, functions, and/or properties disclosed.

As used in this application, an element or step recited in the singular and proceeded with the word "a" or "an" should be understood as not excluding plural of said elements or steps, unless such exclusion is stated. Furthermore, references to "one embodiment" or "one example" of the present disclosure are not intended to be interpreted as excluding the existence of additional embodiments that also incorporate the recited features. Terms such as "first," "second," "third," and so on are used merely as labels, and are not intended to impose numerical requirements or a particular positional order on their objects. The following claims particularly point out subject matter from the above disclosure that is regarded as novel and non-obvious.

The invention claimed is:

1. A method of performing wireless power transfer for a medical device by transferring power from a transmitter unit to a receiver unit, comprising:
providing a charger current from an energy source through a supply line to a transmitter antenna separated by a distance, wherein the distance may vary during the power transfer;
providing a resistance in the supply line by a virtual resistance unit;
generating a modulated magnetic field through the transmitter antenna;
receiving the modulated magnetic field through a receiver antenna of a receiver unit; and
generating a charging current in the receiver unit, wherein the charging current is substantially constant or has a reduced current variation with respect to the varying distance.

2. The method of claim 1, wherein the wireless power transfer from the transmitter unit to the receiver unit is at least one of a parallel resonant inductive wireless power transfer, and a series resonant inductive wireless power transfer.

3. The method of claim 1,
wherein the supply line comprises a DC-DC buck/boost-converter unit and a transmit amplifier unit;
wherein the DC-DC buck/boost-converter unit comprises the virtual resistance unit; and
wherein the virtual resistance unit is connected to the supply line between the DC-DC buck/boost-converter unit and the transmit amplifier unit.

4. The method of claim 1, wherein the charging current is between 50 mA and 150 mA.

5. The method of claim 1, wherein a distance between the transmitter antenna and the receiver antenna is in a predetermined distance range.

6. The method of claim 5, wherein the predetermined distance range includes at least part of a range between 10 mm and 50 mm.

7. The method of claim 5, wherein the resistance is determined such that the rectifier output provides a substantially constant current over the predetermined distance range.

8. The method according to claim 1, wherein the modulated magnetic field is generated such that at least one of a parallel resonant inductive wireless power transfer and a series resonant inductive wireless power transfer is performed.

9. The method according to claim 1,
wherein the method is performed by a system operable to transfer, between the transmitter unit the receiver unit, at least one of: power, and a signal;
wherein the transmitter unit comprises the energy source, the transmitter antenna, and the supply line coupling energy source to the antenna; and
wherein the receiver unit comprises the receiver antenna and a rectifier output;
wherein the transmitter antenna and the receiver antenna are operable to provide a wireless power transfer link; and
wherein the supply line comprises the virtual resistance unit; and
wherein the virtual resistance unit is operable to provide a resistance.

10. The method of claim 9, wherein the resistance is a non-linear resistance in the supply line.

11. The method of claim 9, comprising:
charging a battery of an implantable medical device with the charging current.

12. The method of claim 11, wherein the battery is charged through the rectifier output.

* * * * *